United States Patent [19]

Leinert et al.

[11] Patent Number: 4,923,889
[45] Date of Patent: May 8, 1990

[54] 1,2-DIAMINO COMPOUNDS, PROCESS FOR THEIR PREPARATION AND PHARMACEUTICAL COMPOSITIONS CONTAINING THEM

[75] Inventors: Herbert Leinert, Heppenheim; Christos Tsaklakidis, Weinheim; Gisbert Sponer, Laudenbach, all of Fed. Rep. of Germany

[73] Assignee: Boehringer Mannheim GmbH, Mannheim, Fed. Rep. of Germany

[21] Appl. No.: 230,947

[22] Filed: Aug. 11, 1988

[30] Foreign Application Priority Data

Aug. 11, 1987 [DE] Fed. Rep. of Germany ....... 3726632

[51] Int. Cl.⁵ ..................... A61K 31/40; C07D 295/08
[52] U.S. Cl. .................................. 514/422; 514/428; 544/238; 544/335; 544/372; 546/281; 548/134; 548/127; 548/143; 548/186; 548/247; 548/255; 548/267.2; 548/374; 548/517; 548/526; 548/527; 548/569; 549/495
[58] Field of Search ............... 548/569, 526; 514/428, 514/422; 549/495

[56] References Cited

U.S. PATENT DOCUMENTS

| | | | |
|---|---|---|---|
| 3,962,238 | 6/1976 | Mauvernay et al. | 548/569 X |
| 4,620,015 | 10/1986 | Stiefel | 548/587 |
| 4,645,778 | 2/1987 | Monteil et al. | 514/428 X |
| 4,727,072 | 2/1988 | Grous et al. | 544/148 X |
| 4,758,563 | 7/1988 | Grous et al. | 514/233.8 |

FOREIGN PATENT DOCUMENTS

WO85/02186  5/1985  PCT Int'l Appl. ................. 514/428

Primary Examiner—Joseph Paul Brust
Attorney, Agent, or Firm—Armstrong, Nikaido, Marmelstein, Kubovcik & Murray

[57] ABSTRACT

Compounds are disclosed, including 2-diethylamino-3-isobutoxy-N-phenyl-N-2-furanyl-methyl-propylamine and compounds of the formula:

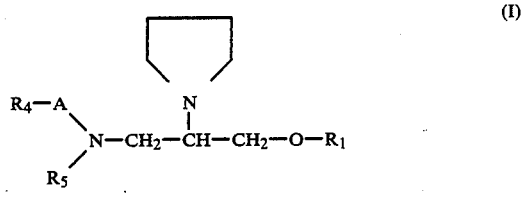

(I)

wherein $R_1$ is an iso-$C_4$-$C_6$-alkyl radical; A is a valency bond or a straight-chained or branched alkyl radical containing up to 6 carbon atoms; $R_4$ is a phenyl radical which is unsubstituted or substituted one or more times by $C_1$-$C_6$-alkyl, $C_2$-$C_6$-alkenyl, $C_1$-$C_3$-alkoxy, $C_2$-$C_6$-alkenyloxy, hydroxy-$C_1$-$C_6$-alkyl, $C_2$-$C_6$-alkylenedioxy, hydroxy-$C_1$-$C_3$-alkoxy, $C_1$-$C_3$-alkoxy-$C_1$-$C_3$-alkoxy, $C_1$-$C_6$-alkylamino, di($C_1$-$C_6$-alkyl)amino, $C_1$-$C_3$-alkoxycarbonyl-$C_1$-$C_3$-alkoxy, $C_1$-$C_6$-alkylthio, $C_1$-$C_6$-alkylsulphinyl, $C_1$-$C_6$-alkylsulphonyl, $C_1$-$C_6$-alkylsulphonyloxy, carboxyl, $C_1$-$C_3$-alkoxycarbonyl, aminocarbonyl, mono- or di($C_1$-$C_6$-alkyl)aminocarbonyl, halo-$C_1$-$C_6$-alkyl, cyano, or halogen; and $R_5$ is a benzyl radical substituted at least once by $C_1$-$C_3$-alkoxy. The compounds are useful for the treatment of heart circulatory diseases.

9 Claims, No Drawings

1,2-DIAMINO COMPOUNDS, PROCESS FOR THEIR PREPARATION AND PHARMACEUTICAL COMPOSITIONS CONTAINING THEM

The present invention is concerned with new 1,2-diamino compounds, processes for the preparation thereof and pharmaceutical compositions containing them.

The new 1,2-diamino compounds according to the present invention are compounds of the general formula:

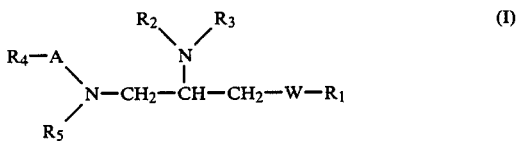

wherein $R_1$ is a straight-chained or branched $C_1$–$C_{12}$-alkyl radical or a $C_3$–$C_7$-cycloalkyl or $C_3$–$C_7$-cycloalkylmethyl radical, W is an oxygen or sulphur atom or a valency bond, $R_2$ and $R_3$, which can be the same or different, are straight-chained or branched, saturated or unsaturated $C_1$–$C_6$-alkyl radicals which are optionally substituted by hydroxyl, $C_1$–$C_3$-alkyl or $C_1$–$C_3$-alkoxy-$C_1$–$C_3$-alkoxy or, together with the nitrogen atom to which they are attached, form a saturated or unsaturated ring which can contain further heteroatoms and is optionally additionally substituted by a lower alkyl or lower alkoxy radical or by an oxygen atom, A is a valency bond or a straight-chained or branched alkyl radical containing up to 6 and preferably up to 3 carbon atoms, $R_4$ is a mono- or bicyclic aromatic radical which is unsubstituted or substituted one or more times, in which the substituents can be alkyl, $C_2$–$C_6$-alkenyl, alkoxy, $C_2$–$C_6$-alkenyloxy, hydroxyalkyl, $C_2$–$C_6$-alkylenedioxy, hydroxyalkoxy, alkoxyalkoxy, alkylamino, dialkylamino, alkoxycarbonylalkoxy, alkylthio, alkylsulphinyl, alkylsulphonyl, alkylsulphonyloxy, carboxyl, alkoxycarbonyl, aminocarbonyl, mono- or dialkylaminocarbonyl, haloalkyl or cyano, as well as halogen atoms, such as chlorine, bromine or fluorine, and $R_5$ is a substituted benzyl radical, an unsubstituted or substituted naphthylmethyl radical, an unsubstituted or substituted five- or six-membered mono- or bicyclic hetarylmethyl radical or an unsubstituted or substituted indan-1-yl or indan-2-yl radical or an unsubstituted or substituted tetralin-1-yl or tetralin-2-yl radical, in which the substituents can be alkyl, $C_2$–$C_6$-alkenyl, alkoxy, $C_2$–$C_6$-alkenyloxy, hydroxyalkyl, $C_2$–$C_6$-alkylenedioxy, hydroxyalkoxy, alkoxyalkoxy, alkylamino, dialkylamino, alkoxycarbonylalkoxy, alkylthio, alkylsulphinyl, alkylsulphonyl, alkylsulphonyloxy, carboxyl, alkoxycarbonyl, aminocarbonyl, mono- or dialkylaminocarbonyl, haloalkyl or cyano, as well as halogen atoms, such as chlorine, bromine or fluorine, and wherein $R_5$ can also be an unsubstituted phenyl radical when W is a valency bond or a sulphur atom or A is a methylene radical or $R_4$ is a naphthyl, tetralinyl or indanyl radical, as well as the pharmacologically acceptable salts thereof.

The $C_1$–$C_{12}$-alkyl radical $R_1$ is preferably methyl, ethyl, propyl, isopropyl, butyl, isobutyl, isoamyl, isohexyl, n-hexyl, n-octyl or n-dodecyl and especially isobutyl, isoamyl or isohexyl. As a rule, the $C_3$–$C_7$-cycloalkyl radical is cyclopentyl or cyclohexyl.

$R_2$ and $R_3$ are preferably ethyl, methyl, propyl, allyl or methallyl. Rings which $R_2$ and $R_3$ can form, together with the nitrogen atom to which they are attached, are preferably pyrrolidine or piperidine and especially pyrrolidine. The heteroatoms which the rings can contain are nitrogen, sulphur or oxygen. There are hereby to be understood, for example, rings such as piperazine, morpholine and thiomorpholine. Substituents of the above-mentioned rings are, in particular, $C_1$–$C_3$-alkyl and $C_1$–$C_3$-alkoxy radicals, for example methyl, ethyl, propyl, methoxy, ethoxy and propoxy. As a rule, the oxygen substituent, together with the carbon atom to which it is attached, represents a carbonyl group. Corresponding rings are, for example, the pyrrolidinone and piperidinone rings.

$R_4$ is a mono- or bicyclic aromatic radical, by which is to be understood phenyl, naphthyl, tetralinyl or indanyl. The alkyl substituents, alone or in combination with other radicals, contain up to 6 and preferably up to 4 carbon atoms and are especially methyl.

Five- and six-membered mono- and bicyclic hetarylmethyl radicals preferably contain, as hetaryl components, pyridyl, pyrimidinyl, pyrazinyl, thienyl, furanyl, pyrazolyl, imidazolyl, tetrazolyl, oxazolyl, isoxazolyl, thiazolyl, isothiazolyl, quinolyl, isoquinolyl, benzofuranyl, benzothienyl, benzothiazolyl or indolyl radicals.

The alkyl radicals, alone or in combination with other radicals of substituents of the ring systems of $R_5$ contain up to 6 and preferably up to 4 carbon atoms and are especially methyl. The substitution can be single or multiple.

The compounds of general formula (I) according to the present invention can be prepared in known manner in that (a) a compound of the general formula:

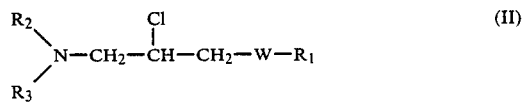

in which $R_1$, $R_2$, $R_3$ and W have the above-given meanings, is reacted with a compound of the general formula:

in which A, $R_4$ and $R_5$ have the above-given meanings; or (b) a compound of the general formula:

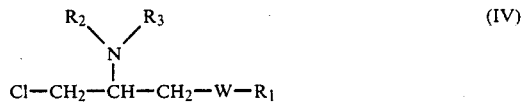

in which $R_1$, $R_2$, $R_3$ and W have the above-given meanings, is reacted with a compound of general formula (III); or (c) a compound of the general formula:

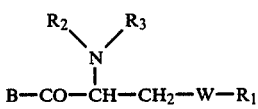
(V)

in which $R_1$, $R_2$, $R_3$ and W have the above-given meanings and B is a halogen atom or an alkoxy radical, is subjected to an amide formation reaction with a compound of general formula (III) and the compound obtained of the general formula:

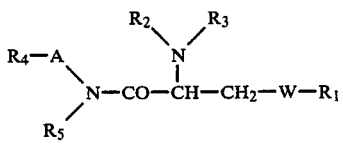
(VI)

in which $R_1$, $R_2$, $R_3$, $R_4$, $R_5$ and W have the above-given meanings, is reduced with a complex hydride or diborane.

The reaction of a compound of general formula (II) with a compound of general formula (II) to give a compound of general formula (I) according to the present invention takes place in known manner in an inert solvent, such as toluene, xylene or dimethylformamide, at ambient temperature or at a temperature of from 40° C. to the reflux temperature of the solvent in the presence of an alkaline condensation agent, for example sodium hydride or sodamide.

The compounds of general formula (II) are known (cf. European Patent Specification No. 0,138,684). They can be prepared in known manner by reacting a compound of the general formula:

$R_1WH$ (VII)

in which $R_1$ has the above-given meaning and W is an oxygen or sulphur atom, with epichlorohydrin and reacting the compound obtained of the general formula:

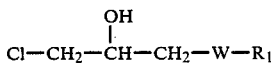
(VIII)

in the presence of aqueous sodium hydroxide solution to give a compound of the general formula:

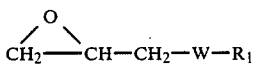
(IX)

The reaction of a compound of general formula (IX) with an amine of the general formula:

$R_2-NH-R_3$ (X)

in which $R_2$ and $R_3$ have the above-given meanings, gives a compound of the general formula:

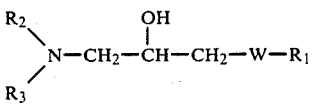
(XI)

in which $R_1$, $R_2$, $R_3$ and W have the above-given meanings.

The reaction of a compound of general formula (XI) with thionyl chloride in the presence of an inert solvent gives a compound of general formula (II).

The reaction of a compound of general formula (IV) with a compound of general formula (III) to give a compound of general formula (I) according to the present invention takes place in an inert solvent, for example toluene or xylene, at a temperature of from 40° C. to the reflux temperature of the solvent in the presence of an alkaline condensation agent, such as sodium hydride or sodamide.

Compounds of general formula (IV) can be prepared by reducing a compound of the general formula:

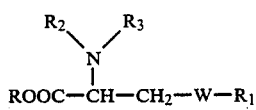
(XII)

in which $R_1$, $R_2$, $R_3$ and W have the above-given meanings and R is an alkyl radical, with a complex hydride, for example lithium aluminum hydride, in an inert solvent in known manner to give a compound of the general formula:

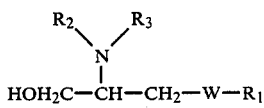
(XIII)

in which $R_1$, $R_2$, $R_3$ and W have the above-given meanings, which is reacted in an inert solvent with thionyl chloride to give a compound of general formula (IV).

The starting compounds of general formula (XII) can be prepared according to the process described in Federal Republic of Germany Patent Specification No. 28 02 864.

The reaction of a compound of general formula (V) with a compound of general formula (III) to give a compound of general formula (VI), as well as the reduction of this compound to give a compound of general formula (I) according to the present invention, takes place according to usual processes, for example by reduction with lithium aluminium hydride or diborane, in an inert solvent, for example diethyl ether or tetrahydrofuran.

The compounds of general formula (V), in which B is a halogen atom, can be prepared by hydrolysing a compound of general formula (XII) and reacting the compound obtained of the general formula:

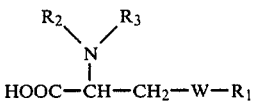
(XIV)

in which $R_1$, $R_2$, $R_3$ and W have the above-given meanings, with a halogenation agent, for example thionyl chloride, in an inert solvent.

The compounds of general formula (III) can be prepared by reducing the corresponding azomethine derivatives or by reducing the corresponding acid amides (cf. Organikum, Organisch-Chemisches Grundpraktikum, 9th edition, Berlin, 1970, p. 736).

The compounds of general formula (I) according to the present invention contain an asymmetric carbon atom. Therefore, the present invention also includes the racemates and the optically-active forms of the compounds of general formula (I) according to the present invention as well as processes for the preparation thereof.

The optically-active compounds can be prepared from their racemic mixtures by known methods via diasteromeric salts. For the racemate resolution, there can be used, for example, tartaric acid, malic acid, camphoric acid, camphorsulphonic acid or dibenzoyltartaric acid.

For converting the compounds of general formula (I) into their pharmacologically acceptable salts, these are reacted, preferably in an organic solvent, with the equivalent amount of an inorganic or organic acid, for example hydrochloric acid, hydrobromic acid, phosphoric acid, cyclamic acid, sulphuric acid, acetic acid, salicylic acid, citric acid, benzoic acid, naphthoic acid, o-acetoxybenzoic acid, adipic acid, maleic acid, oxalic acid or fumaric acid.

The compounds of general formula (I) according to the present invention possess valuable pharmacological properties. They are especially characterised by a blood vessel-relaxing action and can, therefore, be used for the therapy of heart-circulatory diseases.

The new compounds of general formula (I) according to the present invention and the salts thereof can be administered enterally or parenterally in liquid or solid form. As injection medium it is preferred to use water which contains the additives usual in the case of injection solutions, such as stabilising agents, solubilising agents or buffers. Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

Apart from the compounds described in the following Examples, the following compounds are also preferred according to the present invention:

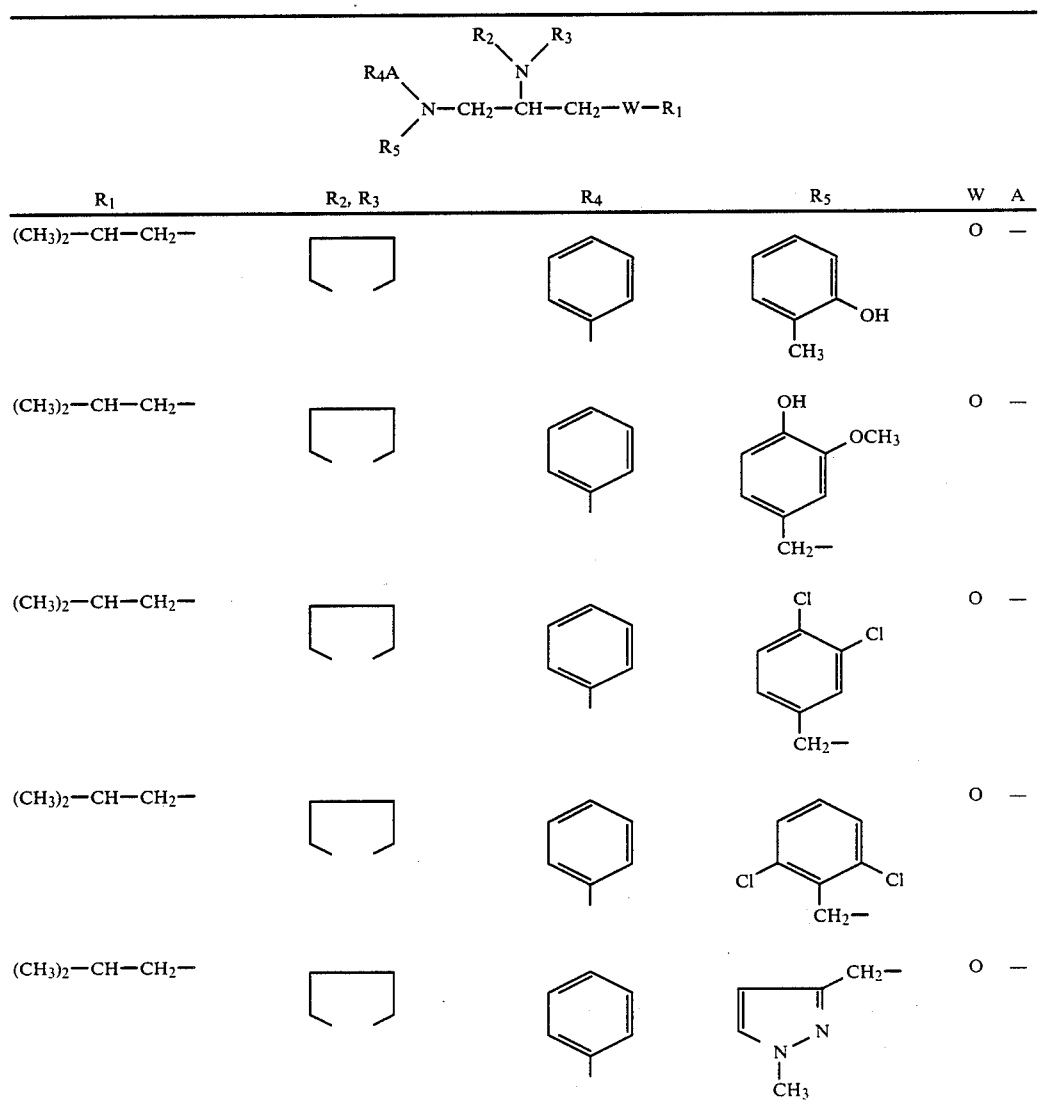

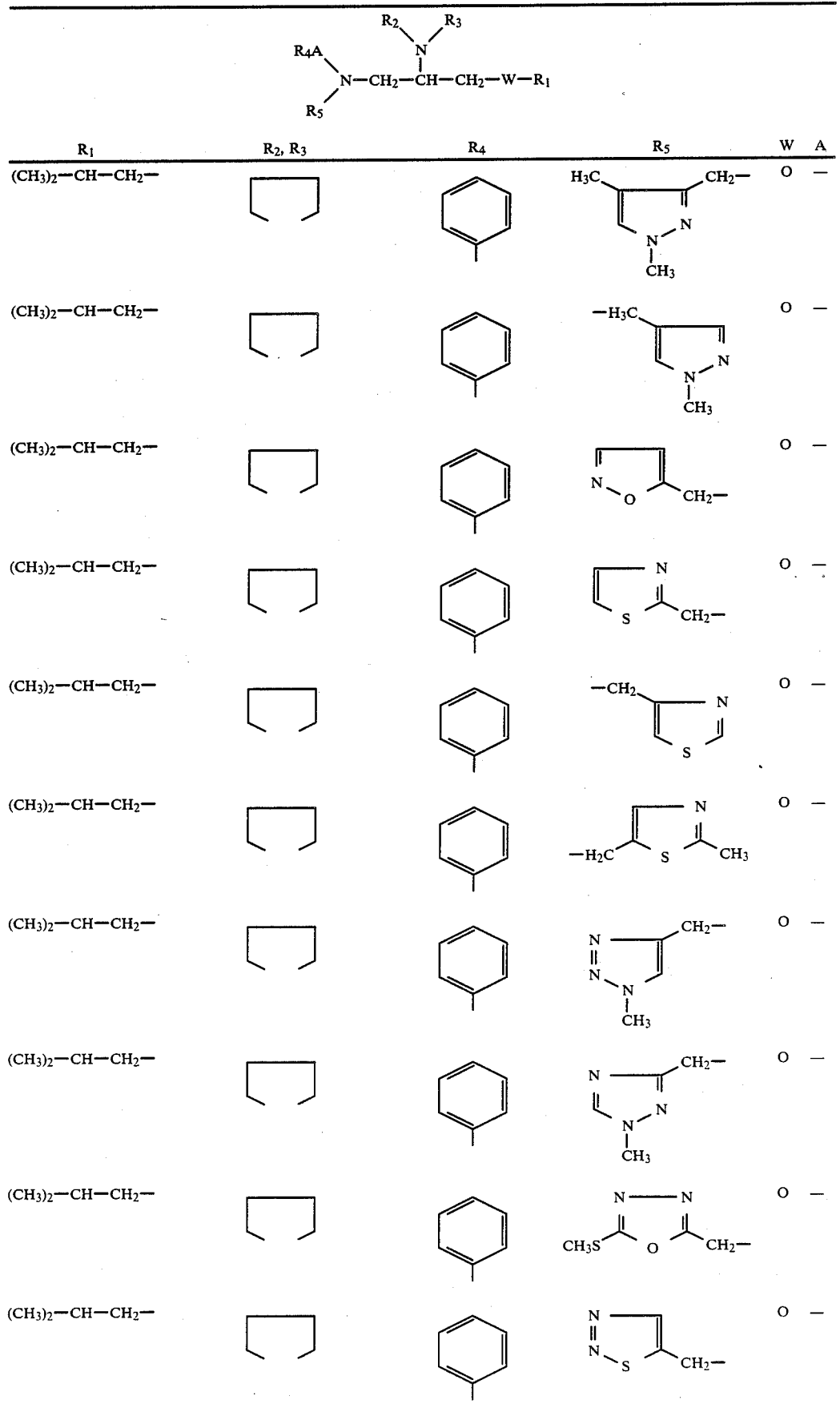

-continued
$$\begin{array}{c} R_2 \quad R_3 \\ R_{4A} \diagdown N \diagup \\ N-CH_2-CH-CH_2-W-R_1 \\ R_5 \end{array}$$
| R₁ | R₂, R₃ | R₄ | R₅ | W | A |
|---|---|---|---|---|---|
| (CH₃)₂—CH—CH₂— |  |  | 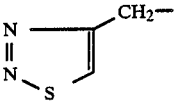 | O | — |
| (CH₃)₂—CH—CH₂— |  |  | 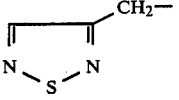 | O | — |
| (CH₃)₂—CH—CH₂— |  |  | 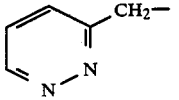 | O | — |
| (CH₃)₂—CH—CH₂— |  |  | 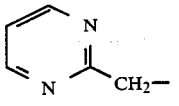 | O | — |
| (CH₃)₂—CH—CH₂— |  |  | 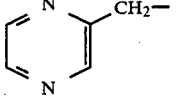 | O | — |
| (CH₃)₂—CH—CH₂— |  |  | 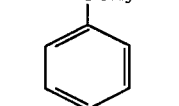 | O | — |
| (CH₃)₂—CH—CH₂— |  |  | 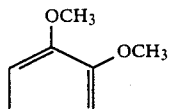 | O | — |
| (CH₃)₂—CH—CH₂— |  |  | 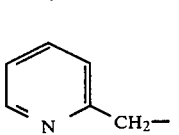 | O | — |
| (CH₃)₂—CH—CH₂— |  |  | 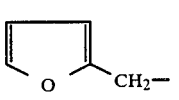 | O | — |
| (CH₃)₂—CH—CH₂— |  |  | 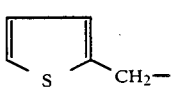 | O | — |

-continued $$\begin{array}{c} R_2 \diagdown \diagup R_3 \\ R_4A \diagdown \phantom{xxx} N \\ \phantom{xx} N-CH_2-CH-CH_2-W-R_1 \\ \diagup \\ R_5 \end{array}$$

| R₁ | R₂, R₃ | R₄ | R₅ | W | A |
|---|---|---|---|---|---|
| (CH₃)₂—CH—CH₂— | pyrrolidino | phenyl | indol-2-ylmethyl (NH) | O | — |
| (CH₃)₂—CH—CH₂— | pyrrolidino | 4-methoxyphenyl | 4-hydroxybenzyl | O | — |
| (CH₃)₂—CH—CH₂— | —CH₂—CH₂—OCH₃<br>—CH₂—CH₂—OCH₃ | 4-methoxyphenyl | 4-methoxybenzyl | O | — |
| (CH₃)₂—CH—CH₂— | —(CH₂)₂—O—(CH₂)₂—OCH₃<br>—(CH₂)₂—O—(CH₂)₂—OCH₃ | 4-methoxyphenyl | 4-methoxybenzyl | O | — |
| (CH₃)₂—CH—CH₂— | CH₃O~~~OCH₃ (cyclic) | 4-methoxyphenyl | 4-methoxybenzyl | O | — |

The following Examples are given for the purpose of illustrating the present invention:

EXAMPLE 1

2-(N-Pyrrolidino)-6-methyl-N-phenyl-N-benzylheptylamine oxalate 34.8 g. Diethyl malonate are added dropwise, with stirring, to a solution of 5.5 g. sodium in 110 ml. anhydrous alcohol. After completion of the addition, the reaction mixture is heated under reflux for 1 hour and then 41 g. 4-methyl-1-bromopentane are added dropwise thereto. The mixture is further heated under reflux for 6 hours and the alcohol then distilled off. The residue is mixed with 100 ml. of concentrated aqueous potassium hydroxide solution and the mixture heated on a waterbath for 2 hours. After cooling, the reaction mixture is acidified with 5N sulphuric acid, then heated under reflux for 3 hours, cooled and extracted with ethyl acetate. The ethyl acetate phase is dried over anhydrous sodium sulphate and evaporated. The residue is distilled in a vacuum; b.p. 120° C./2.5 mm. Hg. The acid obtained (40 g.) is mixed with 50 ml. thionyl chloride and the mixture heated under reflux for 3 hours. It is then evaporated and the residue mixed dropwise at 80° C. with 44 g. bromine, while stirring. After completion of the addition, heating is continued for a further 5 hours. The reaction mixture is then cooled and added dropwise to 100 ml. alcohol. After completion of the addition, reflux heating is continued for 2 hours.

The reaction mixture is cooled and mixed dropwise, while stirring, with 25 ml. pyrrolidine. After completion of the addition, reflux heating is continued for 2 hours and the mixture then evaporated to dryness. For purification, the residue is chromatographed on a silica gel column, 25 g. of an oily residue of ethyl 6-methyl-2-(N-pyrrolidino)-heptanecarboxylate being obtained. This is dissolved in 100 ml. anhydrous tetrahydrofuran and, after the addition of 8 g. lithium aluminum hydride, the mixture is stirred for 3 hours at ambient temperature. Excess lithium aluminium hydride is decomposed by the addition of a concentrated solution of aluminium sulphate and the reaction product is extracted with methylene chloride. The methylene chloride phase is dried over anhydrous sodium sulphate and evaporated, 15.4 g. of an oily residue of 6-methyl-2-(N-pyrrolidino)-heptan-1-ol being obtained.

6 g. of this compound are dissolved in 20 ml. methylene chloride and, after the addition of 8 g. thionyl chloride, the mixture is heated under reflux for 3 hours. It is then evaporated and the residue is dissolved in 20 ml. toluene, mixed with 7 g. N-benzylaniline and 2.8 g. sodium hydride (50% oily suspension) and the mixture heated under reflux for 3 hours. It is then cooled, the reaction solution is mixed with water and the organic layer is separated off. This is dried over anhydrous sodium sulphate and evaporated. For purification, the residue is chromatographed on a silica gel column (elution agent: methylene chloride/2% methanol). The appropriate column fractions are evaporated to give 7.2 g. of an oily residue. This is dissolved in ethyl acetate and mixed with a solution of oxalic acid. The crystals obtained are filtered off with suction and again recrystallised from ethyl acetate. There are obtained 6.5 g. of the title compound; m.p. 125°–126° C.

EXAMPLE 2

2-(N-Pyrrolidino)-3-isobutoxy-N-phenyl-N-(2-methoxybenzyl)-propylamine oxalate 2.4 g. 2-Methoxybenzylaniline, together with 2 g. 2-chloro-1-isobutoxy-3-(N-pyrrolidino)-propane, are dissolved in 20 ml. anhydrous toluene. 0.9 g. Sodium hydride (50% oily suspension) is added thereto and the mixture is heated to 100° C. for 3 hours. It is cooled, mixed with water and the organic layer is separated off. The aqueous phase is again extracted with toluene and the organic phases are combined, dried over anhydrous sodium sulphate and evaporated. The residue is purified by chromatography on a silica gel column (elution agent: methylene chloride/5% methanol). The column fractions are evaporated, the oily residue is dissolved in ethyl acetate and the solution is mixed with a solution of oxalic acid in ethyl acetate. The precipitate obtained is filtered off with suction and again recrystallised from ethyl acetate. There is obtained 1.9 g. of the title compound; m.p. 108° C.

The following compounds are prepared in an analogous manner:

$$\begin{array}{c} R_2 \diagdown \diagup R_3 \\ N \\ R_4-A \diagdown \\ N-CH_2-CH-CH_2-W-R_1 \\ R_5 \diagup \end{array}$$

| Nr. | $R_1$ | $R_2, R_3$ | $R_4$ | $R_5$ | W | A | |
|---|---|---|---|---|---|---|---|
| 3 | $(CH_3)_2CH-CH_2-$ | pyrrolidino | phenyl | 4-($OCH_3$)-benzyl (o-$OCH_3$) | O | — | Oxalate 130° C. ethyl acetate |
| 4 | $(CH_3)_2CH-CH_2-$ | pyrrolidino | phenyl | 4-(CH)-benzyl | O | — | Oxalate 106° C. ethyl acetate |
| 5 | $(CH_3)_2CH-CH_2-$ | pyrrolidino | phenyl | 4-($OCH_2CH=CH_2$)-benzyl | O | — | oil m/e 422 |
| 6 | $(CH_3)_2CH-CH_2-$ | pyrrolidino | phenyl | 4-($O(CH_2)_2CH_3$)-benzyl | O | — | oil m/e 424 |

-continued $$R_4-A-\underset{R_5}{N}-CH_2-\underset{\underset{H}{|}}{C}H-CH_2-W-R_1$$
$$\text{where CH has } -N(R_2)(R_3)$$

| Nr. | R1 | R2, R3 | R4 | R5 | W | A | |
|---|---|---|---|---|---|---|---|
| 7 | $(CH_3)_2CH-CH_2-$ | (pyrrolidine) | phenyl | 2,4-dimethoxybenzyl ($OCH_3$, $OCH_3$) $-CH_2-$ | O | — | oil m/e 426 |
| 8 | $(CH_3)_2CH-CH_2-$ | (pyrrolidine) | phenyl | 2,3-dimethoxybenzyl ($OCH_3$, $OCH_3$) $-CH_2-$ | O | — | Cyclamate 78–80° C. diethyl Ether |
| 9 | $(CH_3)_2CH-CH_2-$ | (pyrrolidine) | phenyl | 3,4,5-trimethoxybenzyl ($CH_3O$, $OCH_3$, $OCH_3$) $-CH_2-$ | O | — | Cyclamate 70° C. diethyl Ether |
| 10 | $(CH_3)_2CH-CH_2-$ | (pyrrolidine) | phenyl | 4-hydroxy-3,5-dimethoxybenzyl ($CH_3O$, OH, $OCH_3$) $-CH_2-$ | O | — | oil m/e 442 |
| 11 | $(CH_3)_2CH-CH_2-$ | (pyrrolidine) | phenyl | 4-chlorobenzyl (Cl) $-CH_2-$ | O | — | Oxalate 140–141° C. ethyl acetate |
| 12 | $(CH_3)_2CH-CH_2-$ | (pyrrolidine) | phenyl | 4-chlorobenzyl (Cl) $-CH_2-$ | O | — | Oxalate 144–145° C. ethyl acetate |
| 13 | $(CH_3)_2CH-CH_2-$ | (pyrrolidine) | phenyl | 4-methylbenzyl ($CH_3$) $-CH_2-$ | O | — | Oxalate 135–136° C. ethyl acetate |
| 14 | $(CH_3)_2CH-CH_2-$ | (pyrrolidine) | phenyl | 4-trifluoromethylbenzyl ($CF_3$) $-CH_2-$ | O | — | Oxalate 129–130° C. ethyl acetate |

-continued

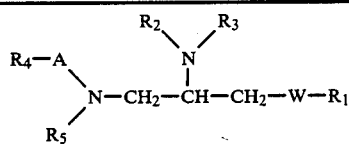

| Nr. | R₁ | R₂, R₃ | R₄ | R₅ | W | A | |
|---|---|---|---|---|---|---|---|
| 15 | (CH₃)₂CH—CH₂— | (pyrrolidine) | 5-indanyl | benzyl (—CH₂—Ph) | O | — | Oxalate 137–138° C. ethyl acetate |
| 16 | (CH₃)₂CH—CH₂— | (pyrrolidine) | phenyl | 1-indanyl | O | — | oil m/e 392 |
| 17 | (CH₃)₂CH—CH₂— | (pyrrolidine) | phenyl | 2-pyridylmethyl | O | — | Oxalate 144–145° C. ethyl acetate |
| 18 | (CH₃)₂CH—CH₂— | (pyrrolidine) | phenyl | 3-pyridylmethyl | O | — | Oxalate 143–144° C. ethyl acetate |
| 19 | (CH₃)₂CH—CH₂— | (pyrrolidine) | phenyl | 4-pyridylmethyl | O | — | oil m/e 367 |
| 20 | (CH₃)₂CH—CH₂— | (pyrrolidine) | phenyl | 2-thienylmethyl | O | — | Oxalate 142° C. ethyl acetate |
| 21 | (CH₃)₂CH—CH₂— | (pyrrolidine) | phenyl | 2-furylmethyl | O | — | Oxalate 132° C. ethyl acetate |
| 22 | (CH₃)₂CH—CH₂— | (pyrrolidine) | phenyl | (5-methyl-2-furyl)methyl | O | — | oil m/e 460 |
| 23 | (CH₃)₂CH—CH₂— | (pyrrolidine) | phenyl | 3-furylmethyl | O | — | oil m/e 446 |
| 24 | (CH₃)₂CH—CH₂— | (pyrrolidine) | phenyl | (2-methyl-3-furyl)methyl | O | — | Oxalate 128° C. ethyl acetate |

-continued

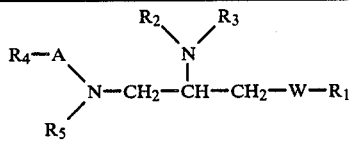

| Nr. | R₁ | R₂, R₃ | R₄ | R₅ | W | A | |
|---|---|---|---|---|---|---|---|
| 25 | (CH₃)₂CH—CH₂— | | phenyl | 1-methyl-pyrrol-2-yl-CH₂— | O | — | oil m/e 369 |
| 26 | (CH₃)₂CH—CH₂— | | phenyl | (4-methyl-isoxazol-5-yl)-CH₂— | O | — | oil m/e 371 |
| 27 | (CH₃)₂CH—CH₂— | | phenyl | (2-methyl-oxazol-4-yl)-CH₂— | O | — | oil m/e 371 |
| 28 | (CH₃)₂CH—CH₂— | | phenyl | (2-methyl-thiazol-4-yl)-CH₂— | O | — | oil m/e 387 |
| 29 | (CH₃)₂CH—CH₂— | | phenyl | benzofuran-5-yl-CH₂— | O | — | oil m/e 406 |
| 30 | (CH₃)₂CH—CH₂— | | phenyl | —CH₂-benzofuran-2-yl | O | — | Oxalate 143–144° C. ethyl acetate |
| 31 | (CH₃)₂CH—CH₂— | | phenyl | benzothiophen-2-yl-CH₂— | O | — | Oxalate 124° C. ethyl acetate |
| 32 | (CH₃)₂CH—CH₂— | | 2-methoxyphenyl | 2-methoxybenzyl | O | — | oil m/e 426 |
| 33 | (CH₃)₂CH—CH₂— | | 4-methoxyphenyl | 2-methoxybenzyl | O | — | oil m/e 426 |
| 34 | (CH₃)₂CH—CH₂— | | 2-methoxyphenyl | 4-methoxybenzyl | O | — | oil m/e 426 |

4,923,889

-continued $$R_4-A-\underset{R_5}{\underset{|}{N}}-CH_2-\underset{\underset{N}{|}}{CH}-CH_2-W-R_1$$
$$\phantom{R_4-A-N-CH_2-}\underset{R_2\phantom{xx}R_3}{}$$

| Nr. | R₁ | R₂, R₃ | R₄ | R₅ | W | A | |
|---|---|---|---|---|---|---|---|
| 35 | (CH₃)₂CH—CH₂— | (pyrrolidine) | 3-methoxyphenyl | 4-methoxybenzyl | O | — | Oxalate 95–96° C. ethyl acetate |
| 36 | (CH₃)₂CH—CH₂— | (pyrrolidine) | 3-methoxyphenyl | 4-hydroxybenzyl | O | — | Hydrochloride 105–106° C. diethyl Ether |
| 37 | (CH₃)₂CH—CH₂— | (pyrrolidine) | 4-methoxyphenyl | 4-methoxybenzyl | O | — | Oxalate 94° C. ethyl acetate |
| 38 | (CH₃)₂CH—CH₂— | (pyrrolidine) | 3,4-dimethoxyphenyl | 4-methoxybenzyl | O | — | Oxalate 104° C. ethyl acetate |
| 39 | (CH₃)₂CH—CH₂— | (pyrrolidine) | phenyl | benzyl | O | —CH₂— | Oxalate 90° C. ethyl acetate |
| 40 | (CH₃)₂CH—CH₂— | (pyrrolidine) | 4-methoxyphenyl | benzyl | O | —CH₂— | oil m/e 410 |
| 41 | (CH₃)₂CH—CH₂— | (pyrrolidine) | 4-methoxyphenyl | 4-methoxybenzyl | O | —CH₂— | oil m/e 440 |
| 42 | (CH₃)₂CH—CH₂— | (pyrrolidine) | 4-fluorophenyl | 4-fluorobenzyl | O | — | Oxalate 97° C. ethyl acetate |

-continued

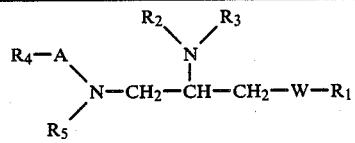

| Nr. | R₁ | R₂, R₃ | R₄ | R₅ | W | A | |
|---|---|---|---|---|---|---|---|
| 43 | (CH₃)₂CH—CH₂— | (pyrrolidine) | 1-naphthyl | benzyl (C₆H₅—CH₂—) | O | — | oil m/e 416 |
| 44 | (CH₃)₂CH—CH₂— | (pyrrolidine) | 2-methoxyphenyl | 2-pyridylmethyl | O | — | oil m/e 397 |
| 45 | (CH₃)₂CH—CH₂— | (pyrrolidine) | phenyl | benzyl | S | — | Oxalate 97–99° C. ethyl acetate |
| 46 | (CH₃)₂CH—CH₂— | (piperidine) | phenyl | 4-methoxybenzyl | O | — | oil m/e 410 |
| 47 | (CH₃)₂CH—CH₂— | (morpholine) | phenyl | 2-thienylmethyl | O | — | oil m/e 388 |
| 48 | (CH₃)₂CH—CH₂— | —C₂H₅ / —C₂H₅ | phenyl | 2-furylmethyl | O | — | oil m/e 358 |
| 49 | (CH₃)₂CH—(CH₂)₂— | (pyrrolidine) | phenyl | 4-methoxybenzyl | O | — | Oxalate 136–137° C. ethyl acetate |
| 50 | (CH₃)₂CH—(CH₂)₃— | (pyrrolidine) | phenyl | 4-methoxybenzyl | O | — | oil m/e 424 |
| 51 | (CH₃)₂CH—CH₂— | (pyrrolidine) | 4-methoxyphenyl | 2-thienylmethyl | O | — | oil m/e 402 |

-continued

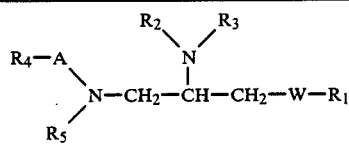

| Nr. | R₁ | R₂, R₃ | R₄ | R₅ | W | A | |
|---|---|---|---|---|---|---|---|
| 52 | (CH₃)₂CH—CH₂— | (pyrrolidine) | 4-OCH₃-C₆H₄— | 2-furyl-CH₂— | O | — | oil m/e 386 |
| 53 | (CH₃)₂CH—CH₂— | (pyrrolidine) | 3-OCH₃-C₆H₄— | 2-(NH-pyrryl)-CH₂— | O | — | oil m/e 385 |
| 54 | (CH₃)₂CH—CH₂— | (pyrrolidine) | 4-OCH₃-C₆H₄— | 3,4-(OCH₃)₂-C₆H₃-CH₂— | O | — | oil m/e 456 |
| 55 | (CH₃)₂CH—CH₂— | (pyrrolidine) | 3,4-(OCH₃)₂-C₆H₃— | 3,4-(OCH₃)₂-C₆H₃-CH₂— | O | — | oil m/e 486 |
| 56 | (CH₃)₂—CH—CH₂— | (pyrrolidine) | C₆H₅— | 1,2,3,4-tetrahydronaphth-1-yl | O | — | oil m/e 406 |
| 57 | (CH₃)₂—CH—CH₂— | (pyrrolidine) | 4-(C₆H₅-CH₂-O)-C₆H₄— | 4-OCH₃-C₆H₄-CH₂— | O | — | oil m/e 502 |
| 58 | (CH₃)₂—CH—CH₂— | (pyrrolidine) | 4-OCH₃-C₆H₄— | 4-(C₆H₅-CH₂-O)-C₆H₄-CH₂— | O | — | oil m/e 502 |
| 59 | (CH₃)₂—CH—CH₂— | (pyrrolidine) | 3-OCH₃-C₆H₄— | 2-pyridyl-CH₂— | O | — | oil m/e 397 |

-continued

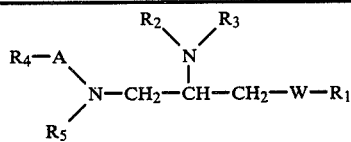

| Nr. | R₁ | R₂, R₃ | R₄ | R₅ | W | A | |
|---|---|---|---|---|---|---|---|
| 60 | $(CH_3)_2-CH-CH_2-$ | (pyrrolidine) | 4-$OCH_3$-phenyl- | 2-pyridyl-$CH_2-$ | O | — | oil m/e 397 |
| 61 | $(CH_3)_2-CH-CH_2-$ | (pyrrolidine) | 2-$OCH_3$-phenyl- | 2-furyl-$CH_2-$ | O | — | oil m/e 386 |
| 62 | $(CH_3)_2-CH-CH_2-$ | (pyrrolidine) | 4-F-phenyl- | 2-thienyl- | O | — | Oxalate 140° C. ethyl acetate |
| 63 | $(CH_3)_2-CH-CH_2-$ | (pyrrolidine) | 4-$CH_3$-phenyl- | indanyl- | O | — | oil m/e 406 |
| 64 | $(CH_3)_2-CH-CH_2-$ | (pyrrolidine) | 4-$OCH_3$-phenyl- | indanyl- | O | — | oil m/e 420 |
| 65 | $(CH_3)_2-CH-CH_2-$ | (pyrrolidine) | 4-F-phenyl- | indanyl- | O | — | oil m/e 410 |
| 66 | $(CH_3)_2-CH-CH_2-$ | (pyrrolidine) | phenyl- | indanyl- | O | — | oil m/e 392 |
| 67 | $(CH_3)_2-CH-(CH_2)_2-$ | (pyrrolidine) | 4-$OCH_3$-phenyl- | 4-$OCH_3$-phenyl-$CH_2-$ | O | — | oil m/e 440 |
| 68 | $C_{10}H_{21}-$ | (pyrrolidine) | phenyl- | 4-$OCH_3$-phenyl-$CH_2-$ | O | — | oil m/e 420 |

-continued

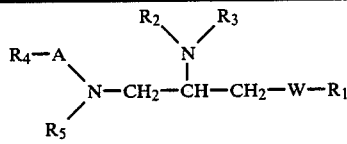

| Nr. | R₁ | R₂, R₃ | R₄ | R₅ | W | A | |
|---|---|---|---|---|---|---|---|
| 69 | $C_{10}H_{21}-$ | (pyrrolidine) | $-C_6H_4-OCH_3$ | $-CH_2-C_6H_4-OCH_3$ | O | — | oil m/e 410 |

In Vitro Test Results

Rat aorta segments were suspended in an organ bath and connected to a force pickup, and stretched to 15 mN. The Krebs-Henseleit solution in the organ bath had the following composition: NaCl=118 mM; KCl=4.7 mM; MgSO₄=1.2 mM; CaCl₂=2.5 mM; KH₂PO₄=1.2 mM; NaHCO₃=25 mM; glucose=11 mM.

The aorta segments were left in the bath for 45 minutes, to reach equilibrium, and then a stock solution of KCl was added to the organ bath to increase the KCl concentration of the nutrient solution in the organ bath to 40 mM. After the aorta segments had been exposed for 30 minutes to the increased potassium concentration, the test substances were added at an identical concentration ($10^{-6}$ mol/liter) to the bath solution. The test substances produced a relaxation effect which varied with the different test substances, and is reported in Table 1 below as a percent of the pre-contraction, determined 25 minutes after the test substance addition to the bath solution. The percent relaxation reported is a measure of the Ca++ antagonistic effect of the respective test substances. The higher the percent relaxation value reported in the right-hand column of Table 1, the more active the substance.

TABLE 1

% relaxation following pre-contration with 40 mM K+ ions.
Incubation time: 25 minutes
Concentration of the test compound: $10^{-6}$ M/liter
Number of tested preparations per substance: n = 4

| Example No. | % relaxation |
|---|---|
| Bepridil (Control) | 51 |
| 21 | 61 |
| 20 | 64 |
| 17 | 62 |
| 35 | 61 |
| 24 | 60 |
| 16 | 61 |
| 37 | 91 |
| 38 | 59 |
| 51 | 66 |
| 3 | 82 |
| 4 | 57 |
| 48 | 72 |
| 49 | 70 |

Bepridil = β-[2-Methylpropoxy)methyl]-N-phenyl-N-(phenylmethyl)-1-pyrrolidineethanamine.

As will be appreciated from Table 1, the compounds of the present invention are cardiovascular agents exhibiting antianginal and antiarrhythemic properties.

The compounds of the present invention may be administered to patients in a suitable amount, generally in an amount of 50 to 1000 mg per dose. The patient will normally be administered from 1 to 3 doses daily. The total daily dosage to the patient will typically be in the range of 1 to 40 mg/kg.

We claim:

1. Compound selected from the group consisting of 2-diethylamino-3-isobutoxy-N-phenyl-N-2-furanyl-methyl-propylamine and a compound of the formula:

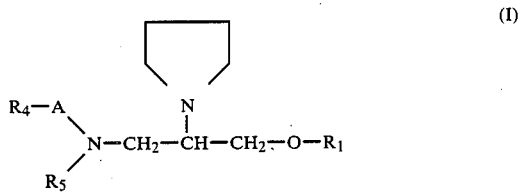

(I)

wherein R₁ is an iso-$C_4$-$C_6$-alkyl radical; A is a valency bond or a straight-chained or branched alkyl radical containing up to 6 carbon atoms; R₄ is a phenyl radical which is unsubstituted or substituted one or more times by $C_1$-$C_6$-alkyl, $C_2$-$C_6$-alkenyl, $C_1$-$C_3$-alkoxy, $C_2$-$C_6$-alkenyloxy, hydroxy-$C_1$-$C_6$-alkyl, $C_2$-$C_6$-alkylenedioxy, hydroxy-$C_1$-$C_3$-alkoxy, $C_1$-$C_3$-alkoxy-$C_1$-$C_3$-alkoxy, $C_1$-$C_6$-alkylamino, di($C_1$-$C_6$-alkyl)amino, $C_1$-$C_3$-alkoxycarbonyl-$C_1$-$C_3$-alkoxy, $C_1$-$C_6$-alkylthio, $C_1$-$C_6$-alkylsulphinyl, $C_1$-$C_6$-alkylsulphonyl, $C_1$-$C_6$-alkylsulphonyloxy, carboxyl, $C_1$-$C_3$-alkoxycarbonyl, aminocarbonyl, mono- or di($C_1$-$C_6$-alkyl)aminocarbonyl, halo-$C_1$-$C_6$-alkyl, cyano, or halogen; and R₅ is a benzyl radical substituted at least once by $C_1$-$C_3$-alkoxy; or a pharmacologically acceptable salt thereof or optical isomer thereof.

2. Compound of claim 1, wherein R₁ is isobutyl or isoamyl.

3. Compound of claim 1, wherein said compound is 2-(N-pyrrolidino)-3-isobutoxy-N-phenyl-N-(4-methoxy-benzyl)propylamine.

4. The compound 2-diethylamino-3-isobutoxy-N-phenyl-N-2-furanyl-methyl-propylamine.

5. Compound of claim 1, wherein said compound is 2-(N-pyrrolidino)-3-isoamyloxy-N-phenyl-N-(4-methoxy-benzyl)propylamine.

6. A pharmaceutical composition suitable for the treatment of heart circulatory diseases comprising a therapeutically effective amount of a compound of claim 1, and a pharmaceutically acceptable carrier.

7. A method of producing a blood vessel relaxing effect in a patient in need of such effect, comprising administering to said patient a blood vessel relaxing amount of a compound of claim 1.

8. Method of claim 7, wherein said relaxing amount is 50 to 1000 mg per dose, administered from 1 to 3 times a day.

9. Compound of the general formula:

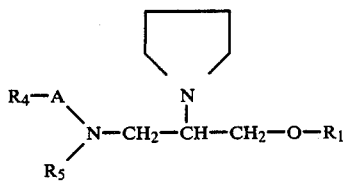

(I)

wherein $R_1$ is an iso-$C_4$–$C_6$-alkyl radical; A is a valency bond or a straight-chained or branched alkyl radical containing up to 6 carbon atoms; $R_4$ is a phenyl radical which is unsubstituted or substituted one or more times by $C_1$–$C_6$-alkyl, $C_2$–$C_6$-alkenyl, $C_1$–$C_3$-alkoxy, $C_2$–$C_6$-alkenyloxy, hydroxy-$C_1$–$C_6$-alkyl, $C_2$–$C_6$-alkylenedioxy, hydroxy-$C_1$–$C_3$-alkoxy, $C_1$–$C_3$-alkoxy-$C_1$–$C_3$-alkoxy, $C_1$–$C_6$-alkylamino, di($C_1$–$C_6$-alkyl)amino, $C_1$–$C_3$-alkoxycarbonyl-$C_1$–$C_3$-alkoxy, $C_1$–$C_6$-alkylthio, $C_1$–$C_6$-alkylsulphinyl, $C_1$–$C_6$-alkylsulphonyl, $C_1$–$C_6$-alkylsulphonyloxy, carboxyl, $C_1$–$C_3$-alkoxycarbonyl, aminocarbonyl, mono- or di($C_1$–$C_6$-alkyl)aminocarbonyl, halo-$C_1$–$C_6$-alkyl, cyano, or halogen; and $R_5$ is a $C_1$–$C_3$-alkoxy substituted benzyl radical; or a pharmacologically acceptable salt thereof or optical isomer thereof.

* * * * *